(12) United States Patent
Abe

(10) Patent No.: US 8,294,751 B2
(45) Date of Patent: Oct. 23, 2012

(54) ELECTRONIC ENDOSCOPE SYSTEM

(75) Inventor: Kazunori Abe, Saitama (JP)

(73) Assignee: Fujinon Corporation, Saitama (JP)

( * ) Notice: Subject to any disclaimer, the term of this patent is extended or adjusted under 35 U.S.C. 154(b) by 1530 days.

(21) Appl. No.: 11/528,662

(22) Filed: Sep. 28, 2006

(65) Prior Publication Data

US 2007/0070193 A1   Mar. 29, 2007

(30) Foreign Application Priority Data

Sep. 29, 2005   (JP) ................................ 2005-283497

(51) Int. Cl.
  *H04N 13/00*   (2006.01)
(52) U.S. Cl. ........................................................ 348/45
(58) Field of Classification Search .................... 348/45, 348/72, 77, 65
  See application file for complete search history.

(56) References Cited

U.S. PATENT DOCUMENTS

| | | | | | |
|---|---|---|---|---|---|
| 3,792,195 | A | * | 2/1974 | Wilson et al. | 348/184 |
| 4,633,304 | A | | 12/1986 | Nagasaki | |
| 5,796,283 | A | * | 8/1998 | Martin | 327/218 |
| 5,796,783 | A | * | 8/1998 | Crawford | 375/298 |
| 5,929,899 | A | * | 7/1999 | Takahashi et al. | 348/65 |
| 7,035,292 | B1 | * | 4/2006 | Giorgetta et al. | 370/509 |
| 2004/0225190 | A1 | * | 11/2004 | Kimoto et al. | 600/177 |
| 2005/0049461 | A1 | * | 3/2005 | Honda et al. | 600/160 |
| 2006/0004253 | A1 | | 1/2006 | Shigemori et al. | |

FOREIGN PATENT DOCUMENTS

JP   2001-46334 A   2/2001

* cited by examiner

*Primary Examiner* — David Czekaj
*Assistant Examiner* — Tracy Li
(74) *Attorney, Agent, or Firm* — Birch, Stewart, Kolasch & Birch, LLP

(57) ABSTRACT

An electronic endoscope system comprises an electronic endoscope and a processor. The electronic endoscope includes a parallel/serial converter which encodes a vertical synchronizing signal and a horizontal synchronizing signal to synchronization codes representing ON/OFF states thereof expressed by several maximum and minimum signal levels for representing the digital image signals, and uses a maximum and a minimum signal levels except the signal levels representing the synchronization codes to express the digital image signals which would normally be represented by the signal levels representing the synchronization codes, while the image signals whose levels are not in the signal levels representing the synchronization codes are not subject to change. The processor includes a synchronizing signal decoder for decoding the vertical synchronizing signal and the horizontal synchronizing signal based on the synchronization codes.

7 Claims, 4 Drawing Sheets

ELECTRONIC ENDOSCOPE SYSTEM

BACKGROUND OF THE INVENTION

1. Field of the Invention

The present invention relates to an electronic endoscope system constituted of an electronic endoscope and a processor between which signals are transmitted and received via radio waves.

2. Description of the Related Arts

Conventionally, medical diagnoses using electronic endoscopes are widely performed. In the electronic endoscope, an imaging sensor such as a CCD is incorporated in a front end portion of an insertion section for being inserted into a body cavity. Image signals obtained by the CCD are subject to signal processing in a processor to display an image of the body cavity, that is, an endoscopic image, on a monitor.

The conventional electronic endoscope and the processor are connected through a signal cable. However, a wireless electronic endoscope system is devised which transmits and receives the signals via radio waves without using the signal cable to improve operability of the electronic endoscope (see U.S. Pat. No. 4,633,304 and Japanese Patent Laid-Open Publication No. 2001-046334). In each reference, a modulating section for modulating the signals and a transmitter for transmitting the signals via the radio waves are provided in the electronic endoscope, and a receiver for receiving the radio Waves and a demodulating section for demodulating the radio waves into the original signals are provided in the processor.

The conventional electronic endoscope with the signal cable requires approximately 4 kV of dielectric strength voltage between a patient circuit in the electronic endoscope and a secondary circuit in the processor. However, such high dielectric strength voltage is unnecessary in the wireless electronic endoscope system since the signal cable is not used between the electronic endoscope and the processor.

In the wireless electronic endoscope system, since the processor receives image signals obtained by the electronic endoscope to display the endoscopic image on the monitor, synchronization between the electronic endoscope and the processor is needed.

However, in the conventional electronic endoscope systems, there is a need to use two channels of frequency bands, because the image signals and the synchronizing signals are transmitted in separate frequency bands.

SUMMARY OF THE INVENTION

A main object of the present invention is to provide an electronic endoscope system in which both image signals and synchronizing signals can be transmitted in a single frequency band and the synchronizing signals can be surely detected.

In order to achieve the above and other objects, an electronic endoscope system of the present invention is constituted of an electronic endoscope and a processor.

The electronic endoscope includes an imaging sensor, an A/D converter, a synchronizing signal encoder, a modulating section and a transmitter. The imaging sensor obtains an image of an observation area of a subject and outputs analog image signals. The A/D converter converts the analog image signals into digital image signals. The synchronizing signal encoder encodes a vertical synchronizing signal and a horizontal synchronizing signal into synchronization codes representing ON/OFF states thereof expressed by several maximums and minimums of signal levels for representing the digital image signals, and uses a maximum and a minimum signal levels except the signal levels except the signal levels representing the synchronization codes to express the digital image signals which would normally be represented by the signal levels representing the synchronization codes, while the image signals whose levels are not in the signal levels representing the synchronization codes are not subject to change. The modulating section applies a digital quadrature modulation to the synchronization codes and the image signals to generate RF signals. The transmitter transmits the RF signals to the processor as a radio wave.

The processor includes a receiver, a demodulating section, a synchronizing signal decoder and an image signal processing section. The receiver receives the RF signals transmitted from the transmitter. The demodulating section demodulates the RF signals into the image signals by digital quadrature detection. The synchronizing signal decoder decodes the vertical synchronizing signal and the horizontal synchronizing signal based on the synchronization codes. The image signal processing section generates an endoscopic image from the image signals.

According to the electronic endoscope system of the present invention, since the electronic endoscope includes the synchronizing signal encoder which encodes a vertical synchronizing signal and a horizontal synchronizing signal into synchronization codes representing ON/OFF states thereof expressed by several maximums and minimums of signal levels for representing the digital image signals, and uses a maximum and a minimum signal levels except the signal levels representing the synchronization codes to express the digital image signals which would normally be represented by the signal levels representing the synchronization codes, while the image signals whose levels are not in the signal levels representing the synchronization codes are not subject to change, and the processor includes the synchronizing signal decoder which decodes the vertical synchronizing signal and the horizontal synchronizing signal based on the synchronization codes, both the image signals and the synchronizing signals can be transmitted in a single frequency band and the synchronizing signals can be surely detected.

BRIEF DESCRIPTION OF THE DRAWINGS

The above and other subjects and advantages of the present invention will become apparent from the following detailed description of the preferred embodiments when read in association with the accompanying drawings, which are given by way of illustration only and thus are not limiting the present invention. In the drawings, like reference numerals designate like or corresponding parts throughout the several views, and wherein.

DETAILED DESCRIPTION OF THE PREFERRED EMBODIMENTS

Figure 1:
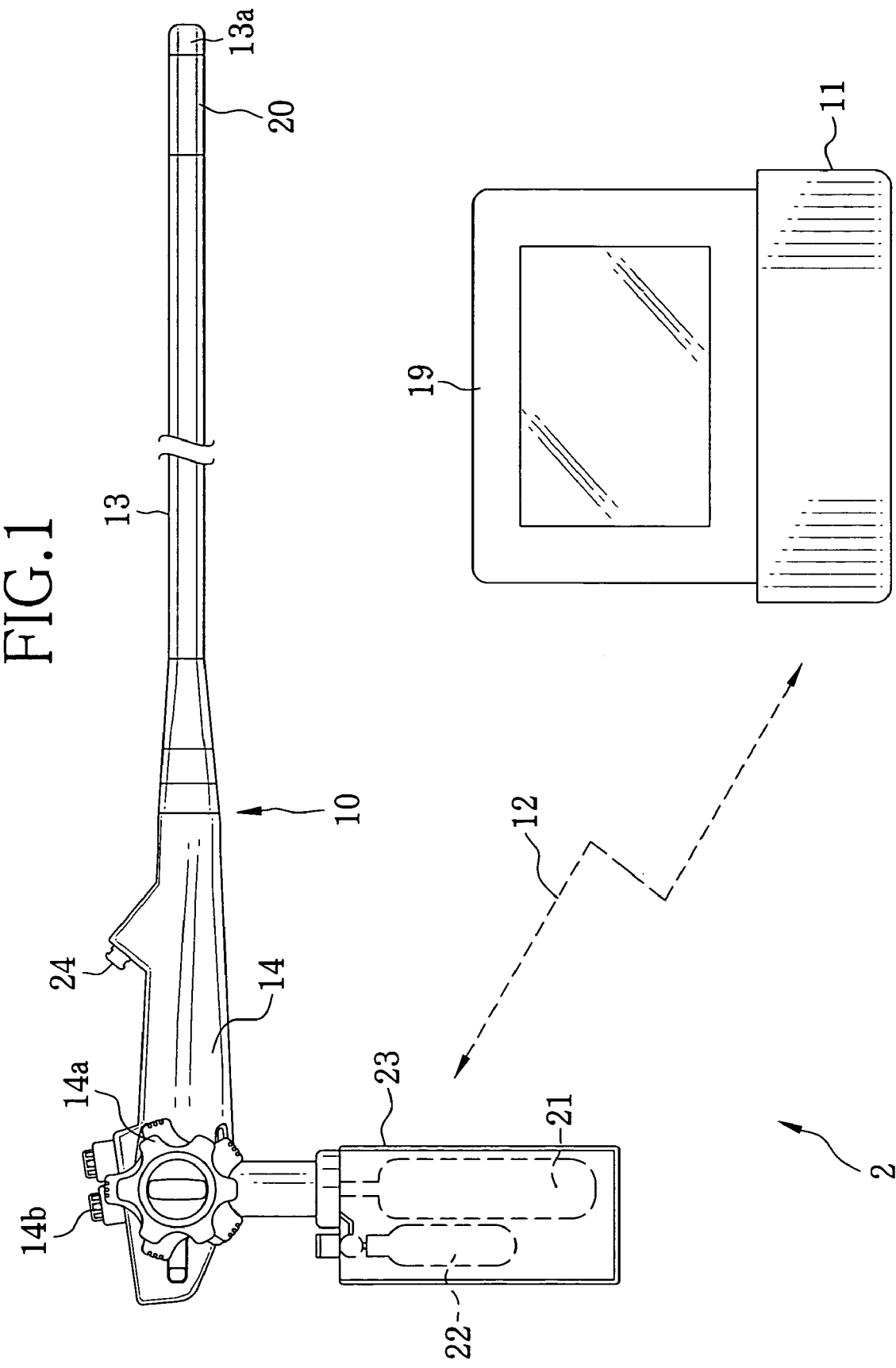
FIG. 1 is a schematic view illustrating a configuration of an electronic endoscope system of the present invention.

In FIG. 1, an electronic endoscope system 2 is constituted of an electronic endoscope 10 and a processor 11. Signals are transmitted between the electronic endoscope 10 and the processor 11 via radio waves 12.

The electronic endoscope 10 is provided with an insertion section 13 inserted into a body cavity, and an operating section 14 connected to a base end portion of the insertion section 13. A front end section 13a of the insertion section 13 incorporates an objective lens 15 for taking image light of an observation area in the body cavity, a CCD 16 (for example, a number of pixels is 1280×960 and a frame rate is 30 frames/second) which is an image sensor for capturing the image of the observation area in the body cavity, and an illumination lens 17 and an LED light source (hereinafter, an LED) 18 for illuminating inside the body cavity (see FIG. 2). The image of the body cavity taken by the CCD 16 is displayed as an endoscopic image on a monitor 19 connected to the processor 11.

Behind the front end section 13a, there is a flexible section 20 formed of plural joint pieces. A wire extending through the insertion section 13 is pushed and pulled by operating an angle knob 14a provided in the operating section 14 to bend the flexible section 20 in the up, down, right and left directions. Thus, the front end section 13a can be directed toward a desired direction inside the body cavity.

A cartridge 23 incorporating a water tank 21 and an air cylinder 22 is attached to a bottom portion of the operating section 14 in a removable manner. Water is stored in the water tank 21 and air is stored in the air cylinder 22. When a water/air supply button 14b in the operating section 14 is operated, the water in the water tank 21 and the air in the air cylinder 22 are respectively supplied through a water pipe and an air pipe and ejected from a washing nozzle (not shown) formed in the front end section 13a to the objective lens 15. Thereby, dirt adhered to a surface of the objective lens 15 is removed and the air is supplied to the body cavity. Since the cartridge 23 is attached to a position where a part of a hand of an operator contacts when the operator grips the electronic endoscope 10, the cartridge 23 helps to ensure a solid operation of the electronic endoscope 10. Note that a numeral 24 is a forceps opening into which a treatment tool is inserted.

Figure 2:
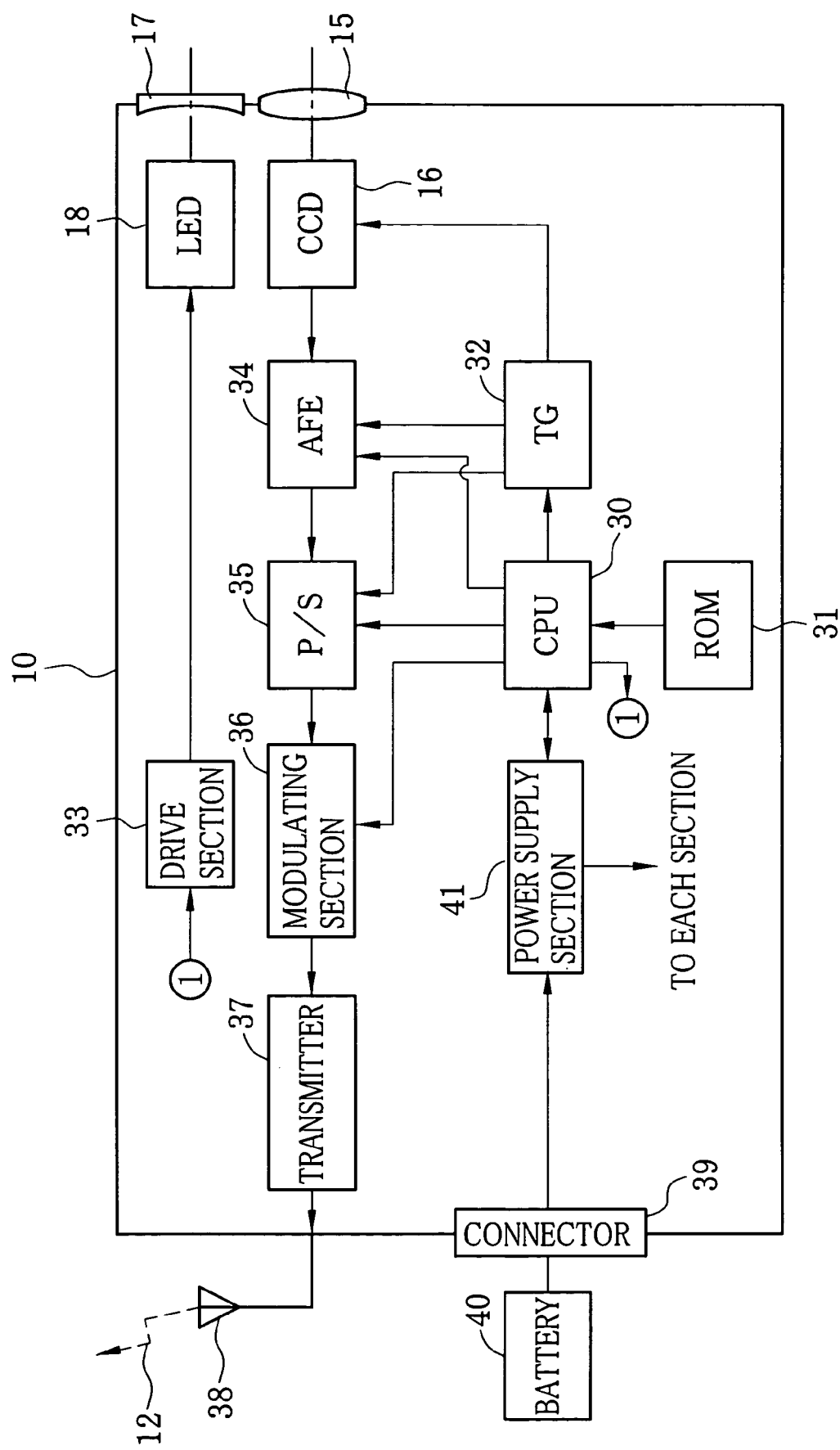
FIG. 2 is a block diagram illustrating a composition of an electronic endoscope.

In FIG. 2, a CPU 30 controls overall operation of the electronic endoscope 10. The CPU 30 is connected to a ROM 31 which stores various programs and data for controlling the operation of the electronic endoscope 10. The CPU 30 reads necessary program and/or data from the ROM 31 to control the operation of the electronic endoscope 10.

In addition, a timing generator (TG) 32 is connected to the CPU 30. The TG 32 is connected to the CCD 16, an AFE 34 and a parallel/serial converter (P/S) 35 which are described later, and sends timing signals (clock pulses) to these components. The CCD 16, the AFE 34 and the P/S 35 operate based on the timing signals from the TG 32.

A drive section 33 is connected to the LED 18. The drive section 33 drives the LED 18 under control of the CPU 30. The light emitted from the LED 18 illuminates the observation area in the body cavity through the illumination lens 17. Note that it is also possible to dispose the LED 18 inside the operating section 14 instead of the front end section 13a. In this case, the light emitted from the LED light source 18 is introduced to the front end section 13a through a light guide.

The CCD 16 converts the image light of the observation area focused through the objective lens 15 onto its image capture surface, and outputs the image signals corresponding to light intensity on each pixel to an AFE 34. The AFE 34 performs correlated double sampling, amplification and A/D conversion to the image signals to convert the analog image signals into digital image signals (10 bit, see FIG. 3).

To the P/S 35, the digital image signals from the AFE 34, and vertical synchronizing signals (VSYNC) and horizontal synchronizing signals (HSYNC) for the image signal, which are produced based on the timing signals from the TG 32, are input.

Figure 3:
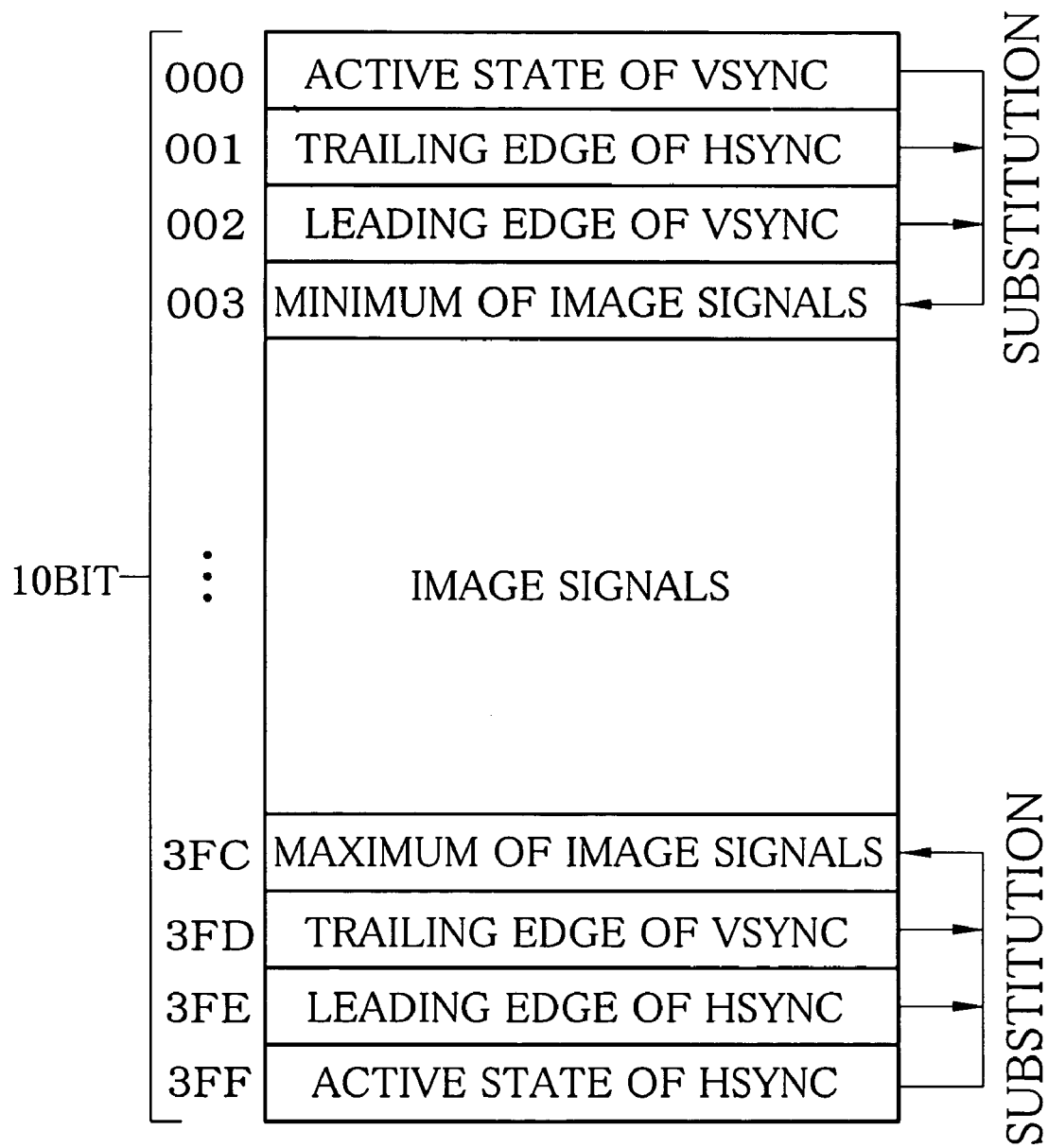
FIG. 3 is an explanatory figure showing a relation between image signals and synchronization codes.

As shown in FIG. 3 in a schematic manner, the P/S 35 encodes the VSYNC and the HSYNC into synchronization codes expressed by signal levels of 10 bit for representing the image signals. As the synchronization codes, "3FF" (in hexadecimal notation, the maximum level of 10 bit) represents an active state of the HSYNC, "3FE" represents a leading edge of the HSYNC, "3FD" represents a trailing edge of the VSYNC, "002" represents a leading edge of the VSYNC, "001" represents a trailing edge of the HSYNC, and "000" (the minimum level of 10 bit) represents an active state of the VSYNC. Then the P/S 35 uses the signal levels "3FC" and "003", which are the maximum and minimum signal levels except the signal levels representing the synchronization codes, to express the image signals which would normally be represented by 3FD to 3FF and 000 to 002.

Then the P/S 35 converts parallel data of the digital image signals and the synchronization codes, into serial data.

A modulating section 36 applies a digital quadrature modulation such as Quadrature Phase Shift Keying (QPSK) to the serial data output from the P/S 35, to generate RF signals. A transmitter 37 transmits the RF signals to the processor 11 as the radio wave 12 through an antenna 38.

A battery 40 is connected to a connector 39. Power of the battery 40 is supplied to each section of the electronic endoscope 10 through a power supply section 41 controlled by the CPU 30. Behind the operating section 14, a battery chamber (not shown) is provided for accommodating the battery 40, and the connector 39 is disposed inside the battery chamber.

Figure 4:
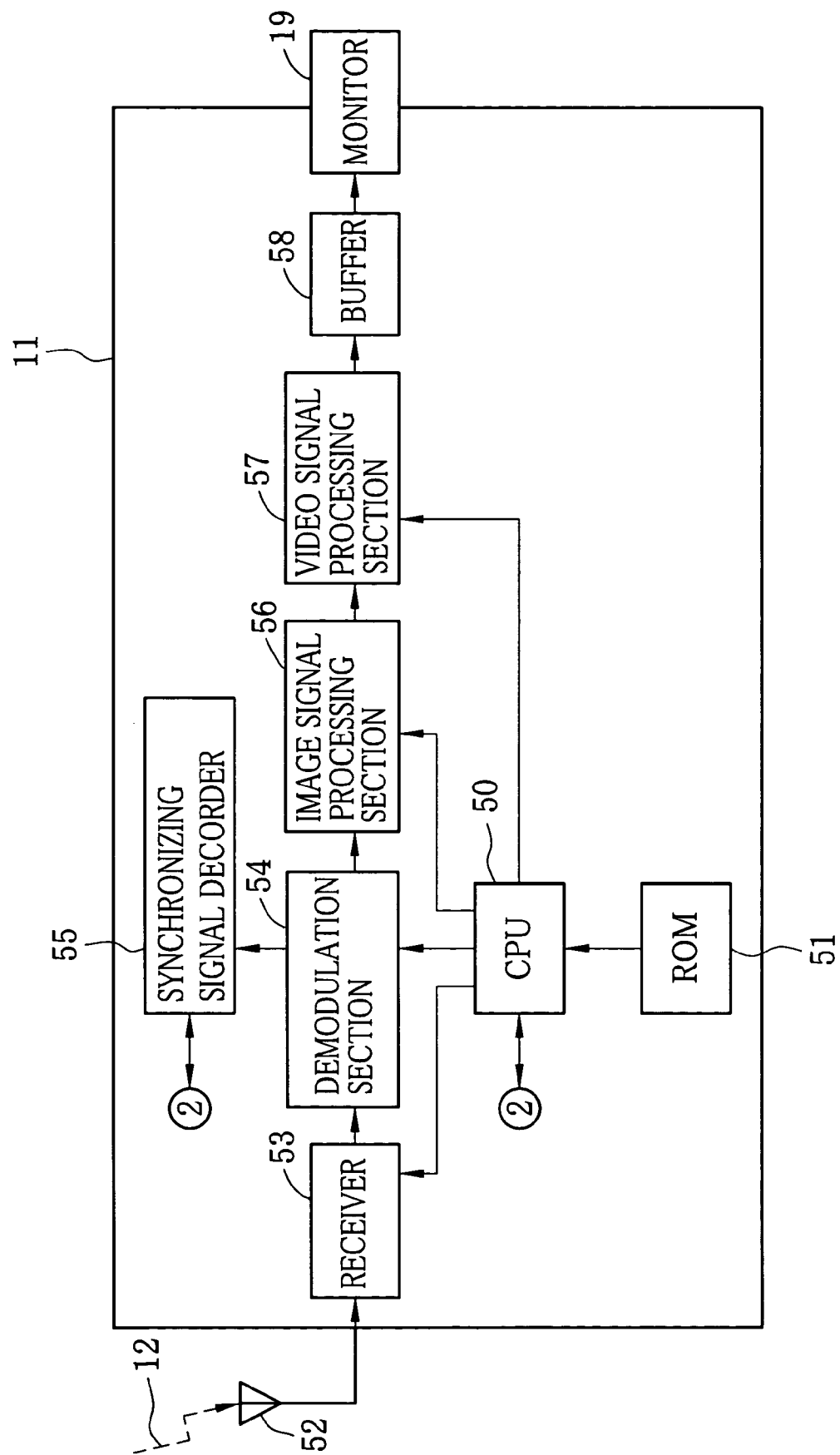
FIG. 4 is a block diagram illustrating a composition of a processor.

In FIG. 4, a CPU 50 controls overall operation of the processor 11. The CPU 50 is connected to a ROM 51 in which various programs and data for controlling the operation of the processor 11 are stored. The CPU 50 reads the necessary program and data from the ROM 51 to control the operation of the processor 11.

An antenna 52 receives the radio wave 12 from the electronic endoscope 10. A receiver 53 amplifies the radio wave 12, that is, the RF signals received through the antenna 52. A demodulating section 54 demodulates the RF signals into the image signals and the synchronization codes by, for instance, the digital quadrature detection.

A synchronizing signal decoder 55 decodes the HSYNC and the VSYNC based on the synchronization codes demodulated by the demodulating section 54, under the control of the CPU 50.

An image signal processing section 56 generates digital video signals from the image signals. A video signal processing section 57 performs image processing such as mask generation and addition of character information to the digital video signals. A buffer 58 temporarily stores the digital video signals which will be displayed on the monitor 19 as the endoscopic image.

To observe the observation area in the body cavity by using the electronic endoscope system 2 configured as above, the insertion section 13 is inserted into the body cavity while the LED 18 is turned on to illuminate the body cavity. The endoscopic image obtained by the CCD 16 is observed on the monitor 19.

At this time, the image light of the observation area in the body cavity entered through the objective lens 15 is focused on the image capture surface of the CCD 16, and thereby the image signals are output from the CCD 16 to the AFE 34. In the AFE 34, the correlated double sampling, the amplification and the A/D conversion are performed to the image signals to convert the analog image signals into the digital image signal.

The digital image signals output from the AFE 34 are converted into the serial data by the P/S 35. In addition, the P/S 35 applies the serial conversion to the VSYNC and the HSYNC for the image signal, which are produced based on the timing signals from the TG 32.

The P/S 35 encodes the VSYNC and the HSYNC into the synchronization codes expressed by the signal levels of 10 bit for representing the image signals. As the synchronization codes, "3FF" represents the active state of the HSYNC, "3FE" represents the leading edge of the HSYNC, "3FD" represents the trailing edge of the VSYNC, "002" represents the leading edge of the VSYNC, "001" represents the trailing edge of the HSYNC, and "000" represents the active state of the VSYNC. Then the P/S 35 uses the signal levels "3FC" and "003", which are the maximum and minimum signal levels except the signal levels representing the synchronization codes, to express the image signals which would normally be represented by 3FD to 3FF and 000 to 002. The image signals in signal levels of 003 to 3FC, which are not for representing the synchronization codes, are subject to the serial conversion directly. Accordingly, a frequency band dedicated for the synchronizing signals is not required, and both the synchronizing signals and the image signals can be transmitted as the radio wave 12 in a single frequency band.

In the modulating section 36, the digital quadrature modulation is performed to the serial data output from the P/S 35 to generate the RF signals. The RF signals are amplified in the transmitter 37 and transmitted to the processor 11 as the radio wave 12 through the antenna 38 of the electronic endoscope 10.

When the processor 11 receives the radio wave 12 through the antenna 52, the received radio wave 12, that is, the RF signal is amplified in the receiver 53. In the demodulating section 54, the digital quadrature detection is performed to the amplified RF signals to demodulate the RF signals and recover the image signals and the synchronization codes generated in the electronic endoscope 10.

The synchronizing signal decoder 55 decodes the HSYNC and the VSYNC based on the synchronization codes demodulated by the demodulating section 54, under the control of the CPU 50. Accordingly, the synchronizing signals can be surely detected.

Thereafter, the image signals are output from the image signal processing section 56 as digital video signals. The output video signals are subject to various image processing in the video signal processing section 57, temporarily stored in the buffer 58, and displayed on the monitor 19 as the endoscopic image.

Note that the signal levels representing the synchronization codes in the above embodiment is merely one example, and the present invention is not limited to this.

Although the present invention has been fully described by the way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic endoscope system composed of an electronic endoscope and a processor, including:
   A. said electronic endoscope including:
      an imaging sensor for obtaining an image of an observation area of a subject and outputting analog image signals;
      an A/D converter for converting said analog image signals into digital image signals;
      a synchronizing signal encoder for encoding a vertical synchronizing signal and a horizontal synchronizing signal into synchronization codes representing ON/OFF states thereof by several maximums and minimums of signal levels for representing said digital image signals, using a maximum and a minimum signal level except said signal levels representing said synchronization codes to express said digital image signals which would normally be represented by said signal levels representing said synchronization codes, and replacing said digital image signals corresponding to said several maximums and minimums with a maximum and a minimum of remaining signal levels, while said image signals whose levels are not in said signal levels representing said synchronization codes are not subject to change;
      a modulating section for applying a digital quadrature modulation to said synchronization codes and said image signals to generate RF signals; and
      a transmitter for transmitting said RF signals to said processor as a radio wave;
   B. said processor including:
      a receiver for receiving said RF signals transmitted from said transmitter;
      a demodulating section for demodulating said RF signals into said image signals by digital quadrature detection;
      a synchronizing signal decoder for decoding said vertical synchronizing signal and said horizontal synchronizing signal based on said synchronization codes; and
      an image signal processing section for generating an endoscopic image from said image signals.

2. An electronic endoscope system claimed in claim 1, wherein said electronic endoscope further includes a timing generator which generates timing signals for producing said vertical synchronizing signal and said horizontal synchronizing signal.

3. An electronic endoscope system claimed in claim 1, wherein said synchronizing signal encoder applies serial conversion to said image signal and said synchronization codes.

4. An electronic endoscope system claimed in claim 1, wherein said synchronization codes include a code showing an active state of said horizontal synchronizing signal, a code showing a leading edge of said horizontal synchronizing signal, a code showing a trailing edge of said vertical synchronizing signal, a code showing a leading edge of said vertical synchronizing signal, a code showing a trailing edge of said horizontal synchronizing signal, and a code showing an active state of said vertical synchronizing signal.

5. An electronic endoscope system claimed in claim 4, wherein said signal level is 10 bit.

6. The electronic endoscope system claimed in claim 5, wherein said synchronization codes are represented by three maximums and three minimums of said signal levels and said digital image signals which would normally be represented by said three maximums and said three minimums are represented by the signal level of 3FC and 003 respectively.

7. The electronic endoscope system claimed in claim 6, wherein said code showing said active state of said horizontal synchronizing signal is represented by the signal level of 3FF, said code showing said leading edge of said horizontal synchronizing signal is represented by the signal level of 3FE, said code showing said trailing edge of said vertical synchronizing signal is represented by the signal level of 3FD, said code showing said leading edge of said vertical synchronizing signal is represented by the signal level of 002, said code showing said trailing edge of said horizontal synchronizing signal is represented by the signal level of 001, and said code showing said active state of said vertical synchronizing signal is represented by the signal level of 000.

* * * * *